United States Patent [19]

Hill

[11] Patent Number: 4,839,008

[45] Date of Patent: Jun. 13, 1989

[54] HOMOGENEOUS CATALYTIC PHOTOCHEMICAL FUNCTIONALIZATION OF ALKANES BY POLYOXOMETALATES

[75] Inventor: Craig L. Hill, Atlanta, Ga.

[73] Assignee: Emory University, Atlanta, Ga.

[21] Appl. No.: 60,337

[22] Filed: Jun. 10, 1987

[51] Int. Cl.$^4$ ............................................. B01J 19/08
[52] U.S. Cl. ............................. 204/157.15; 204/157.6; 204/157.81; 204/157.82; 204/157.87; 204/157.93; 204/158.14
[58] Field of Search ........... 204/157.15, 157.6, 157.61, 204/157.65, 157.75, 157.81, 157.82, 157.87, 157.9, 157.92, 157.93, 158.14

[56] References Cited

U.S. PATENT DOCUMENTS

| | | | |
|---|---|---|---|
| 2,870,171 | 1/1959 | Gable et al. | 549/531 |
| 3,666,777 | 5/1972 | Sorgenti | 549/529 |
| 3,935,272 | 1/1976 | Charpurlat | 568/408 |
| 3,993,672 | 11/1976 | Arzoumanian et al. | 549/533 |
| 4,511,745 | 4/1985 | Bergman et al. | 204/157.75 X |
| 4,522,934 | 6/1985 | Shum et al. | 502/209 |
| 4,562,276 | 12/1985 | Venturello et al. | 556/20 |
| 4,612,301 | 9/1986 | Currie et al. | 502/154 |

OTHER PUBLICATIONS

Renneke, R. F. et al., J. Am. Chem. Soc., vol. 108, No. 12, (1986), pp. 3528–3529.
Smegal, J. A. et al., J. Am. Chem. Soc., vol. 105, No. 11, (1983), pp. 3515–3521, "Hydrocarbon Functionalization by the (Idosylbenzene)Maganese . . . ".
Hill, Craig et al., J. Am. Chem. Soc., vol. 107, No. 18, (1985), pp. 5148–5157, "Catalytic Photochemical Dehydrogenation of Organic Substrates by . . . ".
Geletii, Yu et al., Ac. Soc. USSR, Kinetika vs. Kataliz, vol. 24, No. 2, pp. 486–489, "Catalytic Ozidation of Alkanes by Molecular Oxidation . . . ".
Yamase, Toshihiro, Research Lab. of Res. Util., (1985), pp. 249–261, "Photochemistry of Polyoxometalates as Homogeneous Photocatalysts . . . ".
Akid, Robert et al., J. Chem. Soc. Dalton Trans., 1985, pp. 395–399, "Heteropolytungstates as Catalysts for the Photochemical Reduction . . . ".
Ward, Michael D. et al., J. Phys. Chem., (1984), vol. 88, pp. 4210–4213, "Photocatalytic Alcohol Dehydrogenation Using Ammonium Heptamolbdate".
Yamase, Toshihiro et al., J. Chem. Soc. Dalton Trans., (1984), pp. 793–799, "Solution Photochemistry of Tetrakis(tetrabutylammonium) . . . ".
Dimotikali, D. et al., Inorganica Chimica Acta, vol. 87, (1984), pp. 177–180, "Photochemistry of Heteropoly Electrolytes: The 1:12 Tungstates".
Papaconstantinou, E., J. Chem. Soc. Comm., (1982), pp. 12–13, "Photocatalytic Oxidation of Organic Compounds Using Heteropoly . . . ".
Papaconstantinou, E. et al., Organica Chimica Acta, vol. 46, (1980), pp. 155–158, "Photochemistry of Heteropoly Electrolytes. The 18-Molybdodiphosphate".
Yamase, Toshihiro, J. Chem. Soc. Dalton Trans., (1986), pp. 1669–1675, "Photoredox Chemistry of Keggin Dodecatungstroborate [BW$_{12}$O$_{40}$]$^{5-}$ . . . ".
Argitis, P. et al., Inorga. Chem., vol. 25, (1986), pp. 4386–4389, "Vanadium-Sensitized Photochemistry of Heteropoly Compounds. Mixed . . . ".
Ioannidis, A. et al., Inorg. Chem., vol. 24, (1985), pp. 439–441, "Photocatalytic Generation of Hydrogen by 1:12 Heteropolytungstates . . . ".
Kozhevnikov, I. V. et al., Russian Chem. Rev., vol. 51, (1982), pp. 1075–1088, "Heteropolyacids in Catalysis".
Papaconstantinou, E., J. Chem. Soc., (1982), pp. 12–13, "Photocatalytic Oxidation of Organic Compounds Using Heteropoly . . . ".
Katsoulis, D. et al., J. Am. Chem. Soc., vol. 106, (1984), pp. 2737–2738, "New Chemistry for Heteropolyanions in Anhydros Nonpolar Solvents . . . ".
Mitsubishi Chem. Ind. Co., Ltd., Chemical Abst., vol. 102, (1985), p. 7251r, "Oxidation Catalyst Compositions".
Moraz, Ya., Chemical Abstract, vol. 99, (1983), p. 63147t, "Synthesis and Some Physiochemical Properties of New Heteropolytungstates".
Ono, Y. et al, Chemical Abstracts, vol. 103, (1985), p. 70606w, "Heteropoly Acids as Solid Acid Catalysts".
Finke, Richard et al., J. Am. Chem. Soc., vol. 106, (1984), pp. 7274–7277, "Trisubstituted Heteropolytungstates a Soluble Metal Oxide Analogues . . . ".
Ortega, F. et al., Inorg. Chem., vol. 23, (1984), pp. 3292–3297, "Polyoxotungstate Anions Containing High–Valent Rhenium. 1. Keggin Anion . . . ".
Finke, Richard et al., J. Am. Chem. Soc., vol. 103, (1981), pp. 1587–1589, "Trivacant Heteropolytungstate Derivatives: The Rational Synthesis, . . . ".
Finke, Richard et al., J. Am. Chem. Soc., vol. 108, (1986), pp. 2947–2960, "Trisubstituted Heteropolytungstates as Soluble Metal Oxide Analogues . . . ".
Weakley, T. et al., J. Inorg. Nucl. Chem., vol. 29, (1967), pp. 2935–2944, "Heteropolyanions Containing Two Different Heteroatoms-I".
Hill, Graig et al., J. Am. Chem. Soc., vol. 108, (1986), pp. 536–538, "Substained Epoxidation of Olefins by Oxygen Donors Catalyzed by . . . ".

(List continued on next page.)

Primary Examiner—T. Tung
Assistant Examiner—Ben C. Hsing
Attorney, Agent, or Firm—Oblon, Fisher, Spivak, McClelland & Maier

[57] ABSTRACT

A method for functionalizing alkanes, which comprises: (a) combining one or a mixture of alkanes with a photochemically active polyoxometalate compound to obtain a reaction medium; (b) allowing said photochemically active polyoxometalate compound to catalyze homogeneously functionalization of said alkane in the presence of visible or ultraviolet light; and (c) obtaining said functionalized alkane from said reaction medium.

16 Claims, No Drawings

OTHER PUBLICATIONS

Alizadeh, Mohammed et al., J. Am. Chem. Soc., vol. 107, (1985), pp. 2662–2669, "A Heteropolyanion with Fivefold Molecular Symmetry that Contains . . . ".

Hanson, Robert et al., J. Organic Chem., vol. 51, (1986), pp. 1922–1925, "Procedure for the Catalytic Asymmetric Epoxidation of Allylic Alcohols in . . . ".

Razenberg, Johannes et al., J. Chem. Soc., vol. 4, (1986), pp. 277–279, "Mechanism of Alkene Epoxidation by a Cytochrome P-450 Model, Effect of . . . ".

Nolte, Roeland et al., J. Am. Chem. Soc., vol. 108, (1986), pp. 2751–2752, "On the Rate-Determining Step in the Epoxidation of Olefins . . . ".

Groves, John et al., J. Am. Chem. Soc., vol. 105, (1983), pp. 6243–6248, "Aliphatic Hydroxylation Catalyzed by Iron Porphyrin Complexes".

Traylor, Patricia et al., J. Chem. Soc. Chem. Commun., (1984), pp. 279–280, "Sterically Protected Hemins with Electronegative Substituents: Efficient . . . ".

Bohman, Ove et al., J. Chem. Soc. Chem. Commun., (1986), pp. 1105–1108, "Studies of the Ion Distribution in the Surface of a Liquid Solution of . . . ".

Stinson, Steve, Chemical & Engineering News—Jun. 2, (1986), p. 24, "Epoxidation Advance May Spur Its Industrial Use".

Sharpless, K. Barry et al., Aldrichimica Acta, vol. 12, No. 4, (1979), pp. 63–73, "Metal-Catalyzed, Highly Selective Oxygenations of Olefins and Acetylenes . . . ".

Zonnevijlle, Frans et al., Inorg. Chem., (1972), vol. 21, pp. 2742–2750, "Preparation and Characterization of Heteropolytungstates Containing . . . ".

Malik, S. et al., J. Inorg. Nucl. Chem., (1970), vol. 32, pp. 3875–3890, "Triheteropolyanions Containing Copper(II), Manganese(II), or Managese(III)".

Baker, Louis et al., J. Am. Chem. Soc., vol. 92:12, (1970), Jun. 17, pp. 3794–3797, "A New Fundamental Type of Inorganic Complex: Hybrid Between Heteropoly . . . ".

Tourne, Claude et al., Chem. Soc. of France Bull., No. 4, (1969), pp. 1124–1136, "Les series d'heteropolyanions de type $XW_{11}$, $XZW_{11}$, $X_2W_{17}$, $X_2ZW_{17}$ . . . ".

Malik, S. et al., Inorg. Phys. Theor., [8/797], (1968), pp. 2647–2650, "Heteropolyanions Containing Two Different Heteroatoms. Part II. Anions . . . ".

Tourne, Claude et al., C. R. Acad. SC., Paris, vol. 266, (1968), pp. 1363–1365, "Constitution des Heteropolyanions. Les Types Strucuraux Dans Les Series . . . ".

Tourne, Claude et al., C. R. Acad. Sc., Paris, vol. 266, (1968), pp. 702–704, "Constitution des Heteropolyanions: Reactive des Series $XW_{11}$, $X_2W_{17}$ . . . ".

Umezawa, Yoshio et al., J.C.S. Chem. Comm., (1978), pp. 1106–1107, "Visible Light-Assisted Electrochemical Reduction of Oxygen at a Platinum . . . ".

Collman, James et al., J. Am. Chem. Soc., (1985), vol. 107, pp. 4343–4345, "Mechanism of Oxygen Atom Transfer from High Valent Iron Porphyrins of . . . ".

HOMOGENEOUS CATALYTIC PHOTOCHEMICAL FUNCTIONALIZATION OF ALKANES BY POLYOXOMETALATES

The National Science Foundation (Grant CHE-8402994) & the Petroleum Research Fund (17938-AC3) provided funds used in making this invention.

BACKGROUND OF THE INVENTION

1. Field of the Invention

This invention relates to homogeneous catalytic photochemical oxidation of alkanes by polyoxometalate catalysts.

2. Discussion of the Background Art

Catalysts are substances which facilitate reactions. At a given temperature, a catalyst accelerates the rate of a reaction. The term "catalyst" in this document is used in accordance with this standard meaning.

Catalysis is broken down into two different and unrelated classes of catalysis: (1) heterogeneous catalysis; and (2) homogeneous catalysis. In heterogeneous catalysis, the reaction mixture contains materials in at least two different physical states. Generally, the catalyst is in the form of a solid, and the substrate and product are in the form of either liquids and/or gases. Heterogeneous catalysis is characterized by high temperatures, high pressures and lower selectivity. This is the form of catalysis typically used in large-scale industrial applications (e.g., oil refining and coal liquefaction).

In homogeneous catalysis the reaction mixture is essentially made up of one physical phase. The catalyst, the substrate and the product are all typically dissolved in the reaction mixture. Homogeneous catalysis is characterized by lower temperatures, lower pressures and higher selectivity as compared to heterogeneous catalysis. It thus requires less energy and can be used on more sensitive substrates which could not withstand the temperature and pressure regimen of heterogeneous catalysis.

Because of the very nature of heterogeneous catalysis and heterogeneous catalysis, catalysts used in heterogeneous catalysis and catalysts used in homogeneous catalysis are considered to be two distinct and different systems in the art of catalysis. A heterogeneous catalyst is essentially always an insoluble solid material designed to withstand the adverse environment of heterogeneous catalysis without loss of its catalytic activity. A heterogeneous catalyst is designed to remain insoluble in the reaction medium to facilitate separation of the catalyst from the rest of the reaction mixture upon completion of the reaction.

Heterogeneous catalysts are typically inorganic materials selected on the basis of their ability to remain insoluble in the reaction medium, and withstand high temperatures and high pressures without change. Examples of typical heterogeneous catalysts include zeolites and transition metals supported on an inorganic matrix.

By contrast, homogeneous catalysts are materials which are selected because of their ability to dissolve in the reaction medium where they exhibit catalytic activity. Homogeneous catalysts are typically materials which, at a molecular level, possess a large organic component. Transition metals coordinated to various organic ligands are typical homogeneous catalysts. Homogeneous catalysts are thus selected on the basis of their ability to dissolve in the reaction medium and to exhibit selective catalytic activity.

Since only a limited number of elements are available, one will, of course, be able to find structurally similar materials used both in heterogeneous and homogeneous catalysts. But this overlap is only accidental, and, in the art of catalysis, a material's catalytic activity in a heterogeneous catalytic environment does not suggest its use in a homogeneous catalytic system, and vice versa.

The partial oxidation of organic substrates using either homogeneous or heterogeneous catalysts is one of the most important processes used to transform organic substrates into desired materials or intermediates used in the production of desired materials. For example, the partial oxidation reaction of hydrocarbons is one of the most applied processes for converting hydrocarbons into valuable chemical intermediates.

Alkanes, the most abundant class of organic materials, could be advantageously used in synthetic organic chemistry if they could be transformed into more reactive and useful molecules. In the past five years, interest in functionalization of saturated hydrocarbons, i.e. alkanes, has become intense, and the number of new processes for functionalizing alkanes has grown enormously. In particular, homogeneous catalytic systems for alkane functionalization have been sought because of their lowered energy consumption and simplicity. Thorough investigations of several homogeneous liquid-phase systems for alkane activation or functionalization at room temperature have been reported. These include organometallic systems that effect stoichiometric alkane C-H bond activation with unusual C-H cleavage selectivies, and metalloporphyrin systems that effect catalytic alkane functionalization with conventional C-H cleavage selectivities. See J. A. Smegal and C. L. Hill, *J. Am. Chem. Soc.*, 1983, 105, 3515 and J. T. Groves and T. E. Nemo, *J. Am. Chem. Soc.*, 1983, 105, 6243. There are now also many examples of organometallic alkane activation systems. The stability of these systems limits their use to only a few turnovers. It is to be noted that these catalysts always include organic groups ligated to a metal ion. The catalysts involved in the present invention, unlike all organometallic and metalloporphyrin species in the literature, contain no oxidizable organic structure in the polyoxometalate portion of the compound. This feature removes the element of oxidative instability which can be the success limiting factor for catalysts. The completely inorganic polyoxometalates of this invention combine the stability advantages of metal oxide and other heterogeneous catalysts with the selectivity and experimental tractability advantages of homogeneous catalysts.

As a separate development, a number of investigators have been investigating the ability of polyoxometalates to oxidize organic molecules. To date, however, these inorganic catalysts have not been used to oxidize or functionalize alkanes.

The polyoxometalates or polyoxoanions have been known for many years, but only recently has interest in these materials increased. To some degree, this is due to the fact that these materials have become more chemically well defined. In addition, since 1977, the polyoxometalates and particularly the heteropoly acids have received increasing attention as reagents or catalysts for redox processes involving organic substrates. The majority of these processes involve the use of the heteropoly acids as heterogeneous catalysts.

In terms of homogeneous processes, the polyoxometalates have generally functioned as catalysts for Pd reoxidation in organic oxidations related to the Wacker reaction. It is now recognized that photoassisted catalysis involving the polyoxometalates with visible or near-ultraviolet light facilitates a number of oxidations that are thermodynamically or kinetically unfavorable in the dark. Recently, the present inventor reported on polyoxometalate-catalyzed photooxidation and photodehydrogenation of organic compounds, in *J. Am. Chem. Soc.*, 1985, 107, 5148–5157. However, in this paper, no alkanes were investigated as substrates.

Geletii and Shilov, in *Kinet. Katal.* 24, 486–489, reported on oxidation of methane in the presence of platinum salts and heteropoly acids. However, Geletii and Shilov clearly indicated that the oxidation of methane was catalyzed by platinum IV rather than by the heteropoly acid. No other alkanes were investigated.

Yamase, in *Yuki Gosei Kagaku Kyokaishi* 43, 249–261, reported on photochemistry of polyoxometalates as homogeneous photocatalysis for redox reactions of various organic compounds. Yamase discloses alkene substrates, but does not disclose the use of alkanes as substrates in his reactions. The alkenes give rise to photodimeric products in relatively high yields, whereas the alkanes involved in the present invention give little if any dimeric coupling products.

The following references are also related to the present invention, but in each case the disclosure therein is different from the present invention in that alkanes are not used as substrates, and further, in most cases, heterogeneous rather than homogeneous catalysis is involved:

1. *J. Chem. Soc. Dalton Trans.* 1985, 395–399 "HeteropolyTungstates as Catalysts for the Photochemical Reduction of Oxygen and Water";
2. *J. Phys. Chem.* 1984, 88, 4210–4213, "Photocatalytic Alcohol Dehydrogenation Using Ammonium Heptamolybdate";
3. *J. Chem. Soc. Dalton Trans.* 1984, 793–799 "Solution Photochemistry of Tetrakis(tetrabutylammonium) Decatungstate(VI) and Catalytic Hydrogen Evolution from Alcohols";
4. *Inorganica Chimica Acta*, 87 (1984) 177–180, "Photochemistry of Heteropoly Electrolytes: the 1:12 Tungstates";
5. *J. Chem. Soc., Chem. Commun.*, 1982, 12–13 "Photocatalytic Oxidation of Organic Compounds using Heteropoly Electrolytes of Molybdenum and Tungsten";
6. *Inorganica Chimica Acta*, 46 (1980) 155–158, "Photochemistry of Heteropoly Electrolytes. The 18-Molybdodiphosphate";
7. *J. Chem. Soc. Dalton Trans.* 1986, 1669–1675 "Photoredox Chemistry of Keggin Dodecatungstoborate $[BW_{12}O_{40}]^{5-}$ and Role of Heterogeneous Catalysis in Hydrogen Formation";
8. *Inorg. Chem.* 1986, 25, 4386–4389, "Vanadium-Sensitized Photochemistry of Heteropoly Compounds. Mixed Molybdo- and Tungstovanadates";
9. *Inorg. Chem.* 1985, 24, 439–441, "Photocatalytic Generation of Hydrogen by 1:12 Heteropolytungstates with Concomitant Oxidation of Organic Compounds";
10. *Russian Chemical Reviews*, 51 (11), 1982, 1705–1088 "Heteropolyacids in Catalysis". This reference pertains to thermal, catalytic, primarily homogeneous, processes.

Currie et al, U.S. Pat. No. 4,612,301 is of interest in connection with the present invention in that it discloses heteropoly acids as catalysts for alcohol conversion. Alkanes are not disclosed as substrates therein.

Bergman et al, U.S. Pat. No. 4,511,745, relates to a process for functionalizing alkanes using an organometallic compound. The organometallic compound is quite different from the catalyst used in the present invention.

In spite of the above publications and patents, there has continued to exist a need for new and improved methods for functionalizing alkanes, particularly methods which give rise to new selectivities, improved yields, or new types of products based on alkanes, as compared to the prior art methods.

SUMMARY OF THE INVENTION

Accordingly, it is an object of the present invention to provide a novel process for homogeneous oxidation of alkanes.

It is yet another object of the present invention to provide a novel process for homogeneous carbon-hydrogen bond activation and functionalization of alkanes.

It is yet another object of the present invention to provide a method for producing alkenes, ketones, and amides from alkanes.

It is yet another object of the present invention to provide a method for producing autoxidation products of alkanes.

It is yet another object of the present invention to provide a method for dehydrogenating alkanes to alkenes with concomitant generation of hydrogen gas.

These and other objects of the present invention have been attained by the discovery that a wide variety of polyoxometalates, acting catalytically, are capable of activating alkanes upon irradiation by visible or ultraviolet light. Moreover, these same catalysts can give rise to a variety of products based on alkanes when the catalytic reactions are carried out in the presence of solvent such as acetonitrile, or are carried out in the presence of oxygen. Further, when catalytic platinum (Pt(0)) is present in the reaction medium the reduced polyoxometalate generates hydrogen gas and is oxidized back to its original form. Reoxidation of the polyoxometalate does not always require the presence of Pt(0). In the cases of the most useful catalysis (the tungstate based materials), reoxidation can occur without Pt(0). However, even in these cases, the hydrogen evolution process is faster in the presence of Pt(0).

The process comprises contacting at least one alkane substrate with a polyoxometalate compound to obtain a homogeneous catalytic reaction medium from which a product corresponding to a functionalized form of the substrate is obtained. The polyoxometalates may have any of a variety of structures which are described in greater detail hereinbelow. The substrates may be any alkane generally, (singly or in admixture with other alkanes), and the reaction may be carried out under an inert atmosphere or in the presence of oxygen, with or without Pt(0), or in the presence of another molecule such as water, acetonitrile or t-butanol.

DETAILED DESCRIPTION OF THE PREFERRED EMBODIMENTS

Catalysts

The catalysts of the present invention are polyoxometalate compounds, also known as polyoxometal complexes. Polyoxometalates are condensed oligomeric aggregates composed primarily of $d^0$ transition metal (TM) ions and oxide ions. Since they do not contain d electrons, they cannot have metal-metal bonding and are consequently not "clusters". With the development of NMR, X-ray crystallography, fast atom bombardment mass spectrometry (FABMS) and other analytical methods for rapid and definitive characterization of such complexes, interest in them has grown tremendously.

There are two classes of polyoxometalates, isopolyoxometalates (also called isopoly anions, isopoly compounds, and isopoly complexes) that contain only $d^0$ TM and oxide ions, and heteropolyoxometalates (also called heteropoly anions, heteropoly compounds and heteropoly complexes) that contain one or more "heteroatoms" in addition to the TM and oxide ions. The heteroatoms are located at well defined sites within the polyoxometalate molecule and can be either non-metal ($P^{5+}$, $Si^{4+}$ etc.) or other TM ions (e.g. $Fe^{3+}$, $Co^{2+}$, etc.). Polyoxometalates only form with a handful of metals: tungsten, $W^{VI}$, molybdenum, $Mo^{VI}$, vanadium, $V^V$, niobium, $Nb^V$, and tantanlum, $Ta^V$. In a previous application by the same inventor, U.S. Ser. No. 010,682, filed Feb. 4, 1987, which is hereby incorporated by reference, transition metal substituted polyoxometalates which contain $d \neq 0$ transition metal ions situated in surface sites (i.e. situated such that at least one or more coordination positions on these exposed metal ions are available for binding organic substrates), are disclosed. In contrast to the polyoxometalates of U.S. Ser. No. 010,682, the present application involves those which are photochemically active. By "photochemically active" is meant the ability of a polyoxometalate in an excited state to oxidize an organic compound. Although some transition-metal-surface-site-substituted polyoxometalates display photochemistry, the principal photochemically active compounds are the parent polyoxometalates. For example, $PW_{12}$ (short for $PW_{12}O_{40}{}^{3-}$) displays a richer photochemistry than $PW_{11}$ (short for $PW_{11}O_{39}{}^{7-}$) or its TM-reconstituted derivatives (e.g. $Mn^{II}PW_{11}O_{39}{}^{5-}$) and the like.

There appear to be two factors that determine whether or not a given polyoxometalate will display photochemistry (photoinduced electron transfer=-photoredox behavior) or not. Equation 1 below illustrates the general process—oxidation of the organic substrate, $SH_2$, and reduction of the polyoxometalates to form $P_{red}$.

$$P^*_{ox} + SH_2 \rightarrow P_{red} + S + 2H^+ \qquad (1)$$

The reduced polyoxometalates, $P_{red}$, have $d^{1-2}$ configurations and are consequently darkly colored. They are generically referred to as "heteropoly blues".

The first factor dictating whether or not a given polyoxometalate will display photochemistry concerns the redox potential of the regular ground state complex. If this potential is too negative, the polyoxometalate is very hard or impossible to reduce in the ground state by conventional reducing agents of all kinds. These complexes are not photoreduced by any organic substrate—they do not have photochemistry. The polyoxometalates of Nb and Ta are in this category. Accordingly, generally, polyoxometalates based on these elements are not useful in the present invention.

The other factor that deals with whether or not a given polyoxometalate will display photochemistry has to do with the molecular arrangement of the $MO_6$ octahedra that make up nearly all polyoxometalates (M=metal, O=oxygen). Polyoxometalates of all kinds are constituted primarily by $MO_6$ units where the $d^0$ TM ion is surrounded by six oxygen atoms. There are two types of these $MO_6$ octahedra: "Type 1" $MO_6$ octahedra that contain only one terminal oxo group with the other five oxygens bridging to other TM ions, and "Type 2" octahedra that contain two terminal oxo groups, with the other four oxygens bridging to other TM ions. Type 1 octahedra are readily reduced, Type 2 octahedra are not. As a consequence, polyoxometalates that contain exclusively or nearly exclusively Type 1 octahedra can be photoreduced by a variety or organic substrates while polyoxometalates that contain exclusively or a predominant number of Type 2 octahedra cannot be photoreduced by organic substrates. Thus, only polyoxometalates of V, Mo and W of certain geometries (containing Type 1 octahedra) are applicable to this application.

The second process of relevance to this application is equation 2, the reoxidation of the $P_{red}$ by the protons, both generated by equation 1, forming hydrogen gas. Equation 2 regenerates $P_{ox}$ completing a catalytic cycle.

$$P_{red} + 2H^+ \longrightarrow P_{ox} + H_2 \qquad (2)$$

$$SH_2 + light\ (h\nu) \xrightarrow{P_{ox}\ =\ catalyst} S + H_2 \qquad (3)$$

The net process (equation 1+equation 2) is equation 3. The reduced forms, $P_{red}$, of the polyoxotungstates (either isopoly or heteropoly compounds) are the most readily oxidized; thus, these polyoxometalates are of greatest potential value with respect to the photochemical oxidation or dehydrogenation or hydrocarbons. The reduced forms, $P_{red}$, of most polymolybdates and all polyvanadates are sufficiently stable that they are incapable of evolving $H_2$ at an appreciable rate if at all. An important caveat here however, is that there may be ways of rendering the $P_{red}$ forms of the polymolybdates and even the polyvanadates capable of hydrogen evolution by altering the charge on the $P_{red}$, decreasing the dielectric constant and hydrogen-bonding ability of the solvent or other factors.

In view of the above considerations, it can be seen that activation and functionalization of alkanes according to the present invention may generally be carried out by any polyoxometalate complex based on vanadium, molybdenum, or tungsten, that have predominantly or exclusively Type 1 $MO_6$ octahedra.

Preferably, a polyoxometalate having any one of the following generalized structures may be used according to this invention:

Any isopoly or heteropoly compound of $V^V$, $Mo^{VI}$, or $W^{VI}$ that contains primarily or exclusively "Type 1" $MO_6$ octahedra. This category includes the following and other parent heteropoly oxometalate compounds:

(i) $[XW_xMo_yV_zO_{40}]Q_aM_b$; wherein $x+y+z=12$
(ii) $[X_2W_lMo_mV_nO_{62}]Q_cM_d$; wherein $l+m+n=18$
or
(iii) $[X_5W_pMo_qV_rO_{110}]Q_eM_f$; wherein $p+q+r=30$ In formulas (i) to (iii) above, the values (a+b) or of (c+d) or of (e+f) add up to the charge on the parent polyoxometalate. Preferably, (a+b)=3+ to 12+, more preferably 3+ to 8+; (c+d)=6+ to 15+, more preferably 6+ to 10+; and (e+f)=14+ to 20+, more preferably 14+ to 15+. See definition of $Q_{a,\ c,\ or\ e}$, $M_{b,\ d,\ or\ f}$, and X below.

In addition, the fragments of the above compounds such as in the case of (i), may be employed:

(iv) $[XW_sMo_tV_uO_{39}]Q_gM_h$; wherein $s+t+u=11$ or (v) $[XW_vMo_wV_{xx}O_{34}]Q_iM_j$; wherein $v+w+xx=9$ or the transition metal reconstituted forms of these fragments, such as in the case of (iv) above;

(vi) $[(M')XW_sMo_tV_uO_{39}]Q_kM_{aa}$; wherein $s+t+u=11$ or (vii) $[XW_vMo_wV_{xx}O_{34}]_2(M')_3Q_{bb}M_{cc}$; wherein $v+w+xx=9$ or (viii) $[XW_{yy}Mo_{zz}V_{ll}O_{34}]_2(M')_4Q_{dd}M_{ee}$; wherein $yy+zz+ll=9$ In formulas (iv) through (vii), the values of $(g+h)$ or of $(i+j)$ or of $(k+aa)$ or of $(bb+cc)$ or of $(dd+ee)$ add up to the charge on the polyoxometalate fragment and M'=a transition metal ion with a d≠0 configuration. Preferably, $(g+h)=7+$ to $15+$, more preferably $7+$ to $8+$; $(i+j)=9+$ to $15+$, more preferably $9+$; $(k+aa)=4+$ to $15+$, more preferably $4+$ to $6+$; $(bb+cc)=10+$ to $18+$, more preferably $12+$; and $(dd+ee)=10+$ to $18+$, more preferably $10+$. The definition of $Q_{g, i, k, bb, or dd}$, $M_{h, j, aa, cc, or ee}$, and X is given below.

The transition metal candidates for M' in formula (vi) include $Ti^{4+}$, $Nb^{5+}$, $Ta^{5+}$, $Cr^{3+}$, $Mn^{3+\ or\ 2+}$, $Re^{7+, 6+, or 5+}$, $Fe^{3+\ or\ 2+}$, $Ru^{4+, 3+, or 2+}$, $Co^{3+\ or\ 2+}$, $Rh^{3+}$, $Ni^{2+}$, $Cu^{2+\ or\ 1+}$, and $Zn^{2+}$. Of these ions, the ones which are d=0 or d=10 ions, e.g. $Ti^{4+}$, $Nb^{5+}$, $Ta^{5+}$, or $Zn^{2+}$, are preferred. The preferred non-metal ion candidates include $Sn^{4+}$, $Ge^{4+}$, $Sb^{5+}$, $Al^{3+}$, $Ga^{3+}$, $In^{3+}$ and $Tl^{3+}$. Of the latter, $Sn^{4+}$ and $Ge^{4+}$ are especially preferred.

The transition metal candidates for M' in formulas (vii) and (viii) include the first row divalent transition metal ions. For both formulas (vii) and (viii), $Mn^{2+}$, $Fe^{2+}$, $Co^{2+}$, $Ni^{2+}$, $Cu^{2+}$ and $Zn^{2+}$ are preferred. For formula (vii), $Ce^{4+}$ is also possible.

In addition to these heteropoly compounds, many isopoly compounds of $W^{VI}$, $Mo^{VI}$, and $V^V$ may be used. In particular (ix) $[H_2W_{12}O_{40}]Q_{ff}M_{gg}$;

(x) $[W_{10}O_{32}]Q_{hh}M_{ii}$;

(xi) $[V_{10}O_{28}]Q_{jj}M_{kk}$.

(xii) $(NH_4^+)_6[Mo_7O_{24}]$

In formulas (ix) to (xi), the values of $(ff+gg)$ or of $(hh+ii)$ or of $(jj+kk)$ add up to the charge of the polyoxometalate. Thus, $(ff+gg)=6+$, $(hh+ii)=4+$, and $(jj+kk)=6+$.

The heteroatom, X, in formulas (i)-(viii) can be one of many transition metal ions or main group ions. When x is a transition metal ion, it is preferably a di or trivalent cation selected from the first row of the transition series of the Periodic Table. X can also preferably be a tetravalent cation selected from column 4A of the Periodic Table, excluding carbon; a pentavalent cation selected from column 5A of the Periodic Table, excluding nitrogen; or a trivalent cation selected from column 3A of the Periodic Table. Most preferably, X is $Co^{2+}$, $Fe^{3+}$ (transition metal ions) or $P^{5+}$, $As^{5+}$, $Si^{4+}$, $Ge^{4+}$, or $B^{3+}$ (main group ions). $P^{5+}$ is the most preferred.

$Q_{a, c, e, g, i, k, bb, dd, ff, hh, or jj}$ is any quaternary ammonium, phosphonium, or arsonium salt $R_4N^+$, $R_4P^+$, or $R_4As^+$ wherein any R group in the molecule is independently a $C_{1-30}$ alkyl group which may be branched, straight, cyclic, or a combination of these, or a $C_{6-30}$ aromatic (e.g. phenyl, benzyl, paratolyl, etc.) group. Examples of R groups which are alkyl groups are methyl, ethyl, 1-propyl, 2-propyl, n-, iso- and sec-butyl, etc.

$M_{b, d, f, h, j, aa, cc, ee, gg, ii, kk}$ can be $H^+$, $NH_4^+$ or any main group, transition metal, lanthanide or stable actinide ion. When $M_{b-kk}$ is a main group ion, it is preferably selected from $Li^+$, $Na^+$, $K^+$, and $Mg^{2+}$. When $M_{b-kk}$ is a transition metal ion, it is preferably selected from $Cr^{3+}$, $Fe^{3+}$, $Fe^{2+}$, $Co^{2+}$, $Co^{3+}$ (low spin), $Ni^{2+}$, and $Zn^{2+}$. When $M_{b-kk}$ is a lanthanide ion, it is preferably selected from $La^{3+}$ and $Eu^{2+}$. Any actinide which is stable may be used. $H^+$, $NH_4^+$, $Li^+$, $Na^+$, $K^+$, and $Mg^{+2}$ are potentially most useful, in the order given. $H^+$ is most preferred.

More preferably, compounds with any of the above formulas (i) through (x) where W (tungsten) is the predominant element may be used as the catalyst. Most preferably, compounds with any of the above formulas (i) through (x) where W is the sole element may be used.

Preferred catalyst compounds are those of formulas (i) or (ii) that contain only W and no Mo or V, and where the counterions Q and M are, respectively, tetra-n-alkyl ammonium salts, $R_4N^+$, wherein R contains greater than 3 carbon atoms, preferably 4–10 carbon atoms, and M is $H^+$ or $Li^+$, such that any combination of Q and M adds up to the charge on the polyoxotungstate.

Also preferred are catalysts of formula (ix) where Q and M are, respectively tetra-n-alkyl-ammonium salts, $R_4N^+$, wherein R is an alkyl group of greater than 3 carbon atoms, preferably 4–10 carbon atoms and M is $H^+$ or $Li^+$ such that any combination of Q and M adds up to the charge on the polyoxotungstate, and the charge is 6.

Also preferred are catalysts of formula (x) where ii=0 and Q is a tetra-n-alkyl-ammonium salt, $R_4N^+$, wherein R is an alkyl group of greater than 3 carbon atoms, preferably 4–10 carbon atoms such that any combination of Q and M adds up to the charge on the polyoxotungstate, and the charge is 4.

A more preferred subset of the catalysts of formulas (i)-(xi) is formula (i) where x=12, y and z=0, a=0, and $M_b=(H^+)_3$; formula (ii) where I=18, m and n=0, c=0, and $M_d=(H^+)_6$.

While not wishing to limit themselves to any specific catalyst compounds, Applicant provides herein a list of certain specific catalysts for purposes of illustration:

$H_3PW_{12}O_{40}$ in any degree of hydration,
$H_3AsW_{12}O_{40}$ in any degree of hydration,
$H_4SiW_{12}O_{40}$ in any degree of hydration,
$H_4GeW_{12}O_{40}$ in any degree of hydration (n-$Bu_4N)_4W_{10}O_{32}$,
$H_5BW_{12}O_{40}$ in any degree of hydration,
$H_6P_2W_{18}O_{62}$ in any degree of hydration,
$(NH_4^+)_6[P_2W_{18}O_{62}]$ in any degree of hydration and
$(NH_4^+)_6[Mo_7O_{24}]$ in any degree of hydration.

Mixtures of one or more of the above catalyst materials may also be employed in the present systems.

A particularly preferred catalyst compound according to this invention is a heteropolytungstic acid with the formula $H_3[PW_{12}O_{40}]\cdot 6H_2O$. The anion of this acid consists of 12 hexavalent tungsten atoms and 40 oxygen atoms arrayed around a central phosphorus.

Included within the definition of the catalytic compounds of the present invention are also the hydrates of the above defined catalyst compounds, e.g. those compounds having 0–50 waters of hydration.

The above catalyst compounds may be prepared by conventional procedures readily apparent or determinable to those skilled in the art. Representative methods of preparation of such polyoxometalate compounds may be found in the following references and the references cited therein, all of which are incorporated herein by reference:

(1) Filowitz, M.; Ho, R. K. C.; Klemperer, W. G.; Shum, W. *Inorg. Chem.* 1979, 18, 93.
(2) Rocchiccioli-Deltcheff, C.; Fouirnier, M.; Franck, R.,; Thouvenot, R. *Inorg. Chem.* 1983, 22, 207.
(3) Massart, R.; Constant, R.; Fruchart, J.-M.; Ciabrini, J-P.; Fournier, M. *Inorg. Chem.* 1977, 16, 2916.
(4) Compounds such as those of formula (iv) and related compounds: Zonnevjille, F.,; Tourne, C. M.; Tourne, G. F. *Inorg. Chem.* 1983, 22, 1198.
(5) Knoth, W. H.; Domaille, P. J.; Harlow, R. L. *Inorg. Chem.* 1986, 25, 1577.
(6) Finke, R. G.; Droege, M.; Hutchinson, J. R.; Gransow, O. *J. Am. Chem. Soc.* 1981, 103, 1587.

Substrates

According to the present invention, any alkane may be used as a substrate. Thus, for example, alkanes containing from 1 to over 100 carbon atoms may be used. These $C_{1-100}$ alkanes may be linear, branched, or cyclized. A preferred group of alkanes are those having from 2 to 50 carbon atoms. Alkanes which are liquids at room temperature are preferred, but those which are solids or gases at room temperature may also be used. If the particular alkane which is used is not liquid when used alone, it may be used in a mixture to be a liquid at reaction conditions.

More preferred are alkanes of about 2 to 14 carbon atoms. The cyclic compounds can have as few as 3 carbon atoms and up to about 12 (cyclododecane) or more carbon atoms in the ring. Preferred cyclic compounds are those with 5 to 12 carbon atoms in the ring. The cylcic compounds can be substituted by either straight or branched chain alkyl groups.

Specific illustrative examples of suitable alkanes which can be used (i.e., alone or in a mixture to produce a liquid at reaction conditions) are:

| | |
|---|---|
| methane | ethane |
| methyl cyclooctane | propane |
| propylcyclooctane | cyclopropane |
| n-nonane | isobutane |
| neooctane | n-pentane |
| n-decane | 2,3-dimethyl pentane |
| neopentane | cyclodecane |
| cyclopentane | 4-methyl decane |
| n-hexane | methyl cyclodecane |
| cyclohexane | n-dodecane |
| 2-methyl hexane | 2-propyl nonane |
| 3-methyl hexane | n-tetradecane |
| methyl cyclohexane | 2-methyl, 4-butyl decane (all isomers) |
| dimethyl cyclohexane | 6-hexyldodecane |
| 2-ethyl hexane | 2-ethyl hexylcyclodecane |
| 2,2'-dimethyl hexane | 1,4-dibutylcyclooctane |
| 2-methyl, 4-ethyl hexane | n-eicosane |
| n-octane | |

The alkanes may be reacted in the presence of other organic molecules to result in final products which are functionalized with the other reactant or moiety derived therefrom. For example, some alkane reactants in the presence of acetonitrile, will result in alkenes, whereas others will react to produce alkyl methyl ketones, and still others will react to produce acetamides. It is expected that other organic reactants which are present in the reaction medium in addition to the alkanes will in some instances also take part in the reaction by reacting with the activated alkane to result in useful products. For example, nitriles, alcohols, acids, ethers, esters, alkenes, arenes, alkynes, aldehydes and organo halides of all kinds could be present. Of these, $C_2$–$C_{12}$ nitriles, alcohols, and carboxylic acids are preferred.

The following Table I shows the three major products of alkane oxidation in the presence of acetonitrile.

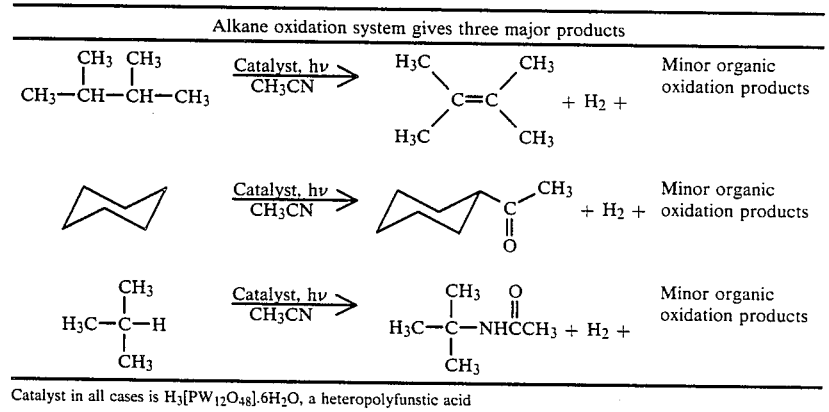

Catalyst in all cases is $H_3[PW_{12}O_{48}]\cdot 6H_2O$, a heteropolyfunstic acid The principal products are methyl ketone, N-alkylacetamide, and alkene, and the product distributions vary greatly with the alkane structure. Substrates with tertiary C-H bonds produce alkane with very high selectivities ($\geqq 90\%$) if the bond is adjacent to another tertiary C—H bond, N-alkylacetamide with very high selectivities ($\geqq 90\%$) if the bond is adjacent only to primary centers, as in the case of isobutane, and a mixture of products if the bond is adjacent to at least one secondary center. All substrates with only secondary C—H bonds (cycloalkanes) yield methyl ketone; in the case of cyclohexane, cyclohexyl methyl ketone (CMK) is the only major oxidation product detectable by GC and GC/MS analysis (>90% selectivity). Most alkanes give little if any alcohol or dimeric coupling products (RR). For these processes, hydrogen, the only detectable reduction product, is generated in an amount approximately equal to the oxidizing equivalents represented by the organic products, providing a reasonable redox balance for the processes. The quantum yields for the production of $P_{red}$ by photooxidation of alkanes are quite high (~0.1 at 350 nm) for the most reactive alkanes, and several turnovers with respect to $P_{ox}$ can be achieved after several hours of irradiation with the light source.

The reaction may also be carried out in the presence of oxygen. If the reactions are run in the presence of air, typical free radical-chain autooxidation products such as alkylhydroperoxide, ketone, or alcohol, depending on the substrate, are produced at the expense of the other products. The $O_2$ reactions are run under exactly the same conditions as the anaerobic reactions except $O_2$ (or, less desirably, air) is substituted for the inert atmosphere (argon or nitrogen).

The reaction may also be carried out in the presence of Pt(0) (i.e. catalytic platinum). If catalytic platinum is present, the reduced polyoxometalate generates hydrogen gas and is oxidized back to its original form.

Also any form of Pt(0) or other noble metal catalyst that is active for catalytic dehydrogenation of organic substrates could be used. The noble metal catalysts, including Pt(0), can either be supported on an inert material such as carbon black, silica or alumina, or present as a support-free finely divided powder or colloidal suspension. The Pt(0) or other noble metal catalyst is included in the reaction medium in a catalytic amount (e.g. 0.001 mole % to 1.0 mole % based on any of the reactants present).

Reaction Conditions

The process of the present invention is directed to the activation and functionalization of alkanes. Generally, the alkane or other hydrocarbon substrate is dissolved in, e.g. acetonitrile solution containing the polyoxometalate catalyst. A catalytic amount of Pt(0) on carbon or other hydrogen evolution catalyst may or may not be added, then the mixture is degassed, placed under an inert gas such as nitrogen or argon, and irradiated with near UV or blue light. Sunlight could also be employed with some catalysts. The wavelength of the radiation may be above about 210 nm, with an upper limit of ca. 400 nm. The products form readily.

In a typical reaction, 10.0 mL of an acetonitrile solution $3.13 \times 10^{-3}$M in polyoxometalate (e.g. $H_3PW_{12}O_{40} \cdot 11H_2O$) and 0.3M in hydrocarbon (e.g. cyclohexane) and 3 mg of 10% Pt(0) on carbon (a hydrogen evolution catalyst) is placed in a 25 mL Schlenk flask (25 mL round-bottom flask equipped with a high-vacuum stopcock side arm). The solution is degassed, placed under nitrogen then irradiated with either sunlight or a 1000 w Xe lamp using a pyrex cutoff filter (the glass of the flask itself can function as this filter). The above amounts are not be interpreted as limiting the invention, but are presented as one possible embodiment of a reaction system.

Several other solvents may be used but they will either be photooxidized themselves or, as in the case of acetonitrile, they will participate in production of the products. These solvents may produce some useful and unprecedented reactions. For example, if a tertiary alcohol such as t-butanol is used as a solvent the substantially higher reactivity of the alkane substrates relative to this alcohol should not decrease the quantum yields for the hydrocarbon functionalization products substantially and the alcohol should be captured by intermediate carbonium ions producing ethers. Similarly, carboxylic acids and a number of other organic solvents may be alkylated by carbonium ion intermediates or react with radical intermediates derived from the hydrocarbons generating a range of products that have incorporated alkyl groups from the reactant hydrocarbon. The polyoxometalate catalyst can be used over a wide range in concentrations from less than $10^{-5}$M to 0.05M or more, preferably ca. 1–5 mM. The hydrocarbon substrate can be used in large excess as in the above case or in comparable concentrations to the polyoxometalate if multifunctionalization is desired. However, the highest product selectivities are achieved under pseudo first-order conditions, (hydrocarbon substrate present in large excess over the catalyst). Yields and selectivities with respect to product formation are increased if the hydrogen is removed as it is formed.

The above steps may be carried out at a superatmospheric or subatmospheric pressure, however atmospheric pressure is preferred because the results at the other pressures generally do not warrant the use of such extraordinary measures.

Extensive screening has revealed that two common solvents, water and acetonitrile, are less reactive in the present systems than the alkane themselves; thus, these solvents are preferably used in alkane functionalization chemistry. It is also expected that other solvents, such as t-butanol, or other solvents which are less reactive than the alkanes, could also be used in the reaction medium. Moreover, as mentioned above, additional organic reactants can be included in the medium even if they are themselves reactive (i.e. oxidized by the catalyst or react with the activated alkane) under the process conditions, if they result in a desired product.

The invention now being generally described, the same will be better understood by reference to certain specific examples which are included herein for purposes of illustration only and are not intended to be limiting of the invention or any embodiment thereof, unless specified.

EXPERIMENTAL EXAMPLES

Materials and Methods

Alkanes and alkenes were reagent grade and purified by chromatography on activity grade I alumina. The acetonitrile was Burdick and Jackson glass distilled grade and used without purification. The heteropolytungstic acid "$H_3PW_{12}O_{30} \cdot nH_2O$" was prepared by the methods of H. Wu, *J. Biol. Chem.* 1920, 43, 189 and P. Souchay, "Ion Minéraux Condensés", Masson et Cie, Paris, 1969, p. 92. Experiments have indicated that the degree of hydration of heteropoly acids can affect various features of the photochemical dehydrogenation of alkanes catalyzed by these compounds. The degree of hydration of the $H_3PW_{12}O_{40} \cdot nH_2O$ was determined precisely to be n=10.7. The most accurate description of this particular catalyst, 1, is probably $[(H_2O)_2H]_3PW_{12}O_{40} \cdot 4.7H_2O$.

The light sources used were Oriel 1000 w Xe lamps equipped with infrared filters and pyrex ($\lambda > 280$ mm) cut-off filters. The UV-visible spectrometer used for kinetics and monitoring various reactions was a microprocessor controlled multidiode array instrument (H/P 8451A). Analysis of the organic products was performed using a H/P Model 5890 gas chromatograph equipped with a H/P 25-m, 5% phenyl-methyl silicone capillary column, flame ionization detectors and a H/P 3390A electronic integrator. Quantification of the hydrogen was carried out using a Varian gas chromatograph equipped a molecular sieve 5A column operated at 50° C. and an integrating strip chart recorder. Product yields were determined using internal standard techniques. The identities of products were confirmed by gas chromatography/mass spectrometry (gc/ms) analysis on either a Finnegan 4000 or a VG 70S instrument. $^1$H NMR spectra were obtained on a Nicolet 360-NB, 360 MHz spectrometer and the $^{183}$W NMR spectra were obtained on a IBM WP200SY spectrometer using a probe specially designed and fabricated (Cryomagnetic Systems) for $^{183}$W NMR spectroscopy on that instrument.

The catalytic photochemical dehydrogenation reactions monitored by electronic absorption spectroscopy were carried out in rectangular pyrex cuvettes equipped with long necks, stopcocks and septum stoppers for removal of gaseous and liquid samples without introduction of air, and micro magnetic stirring bars to facilitate stirring of the sample during irradiation. The other reactions were carried out in 25 mL Schlenk flasks equipped with high vacuum teflon stopcocks. For the reactions run in cuvettes, 2.0 mL of an acetonitrile solution $3.13 \times 10^{-3}$M in heteropolytungstate and 0.3M in alkane were introduced into the reaction vessel. For the reactions run in Schlenk flasks, 10.0 mL of the same acetonitrile solution with 3 mg of Pt(0) on carbon were introduced into the reaction vessel. In all cases, the contents of the reaction vessel were degassed, placed under argon, then irradiated with stirring for the specified times given in the text. Gaseous and liquid aliquots were withdrawn by syringe at various times for gc or gc/ms analysis.

Results and Discussion

General Characteristics of the Reactions

Irradiation ($\lambda > 280$ nm) of acetonitrile solutions of alkanes and the complex, $[(H_2O)_2H]_3PW_{12}O_{40}.4.7H_2O$, 1, with or without a catalytic amount of Pt(0) hydrogen evolution catalyst present, under an inert atmosphere, results in catalytic dehydrogenation of these saturated hydrocarbons. For most branched alkanes, the alkene(s) and hydrogen are the only major products (equation 4). These reactions proceed by two distinct families of processes.

$$\text{alkane} + h\nu \xrightarrow{1} \text{alkene} + H_2 \quad (4)$$

The first is photochemical in nature and involves production of the kinetically competent charge transfer excited state(s), (P* in equations 5 and 6) and the quenching of these excited states by, among other processes, the oxidation of the organic substrate (SH$_2$) (equation 6). These initial photochemical processes result in the conversion of radiant energy into chemical energy. The second family of processes is thermal in nature, also quite complex, and involves transformation of unstable organic intermediates, including both radicals and carbonium ions, into the observed organic products, as well as reduction of the hydrogen ions formed in the photooxidation step by the reduced polyoxometalate (P$_r$) regenerating the starting polyoxometalate (equation 7).

$$P + h\nu \rightarrow P^* \quad (5)$$

$$P^* + SH_2 \rightarrow P_r + S + 2H^+ \quad (6)$$

$$P_r + 2H^+ \rightarrow P + H_2 \quad (7)$$

In the branched alkane dehydrogenation reactions (equation 4), both the absolute product yields and the observed regioselectivity manifested in the product distributions are influenced minimally by the temperature. The degree of hydration of the heteropolytungstic acid catalyst, 1, has a dramatic effect on the solubility of the catalyst, but only a small influence on the product distribution. All reactions were run using as the catalyst, 1, the Keggin heteropolytungstic acid, with a constant amount of hydration (10.7H$_2$O per PW$_{12}$O$_{40}^{3-}$). The absence of the hydrogen activation catalyst, Pt(0) on carbon, decreases the overall rate of catalytic photochemical alkane dehydrogenation by rendering the P$_r$ reoxidation processes, equation 7, rate determining and very slow. The presence of Pt(0) on carbon influences the product distributions in a complex but experimentally reproducible manner. The presence of Pt(0) on carbon decreases the quantity of cyclooctene relative to nonolefinic products generated upon catalytic photochemical dehydrogenation of cyclooctane. However the presence of this catalyst has a minimal effect on the product distributions generated from catalytic dehydrogenation of most of the branched alkanes, where alkenes already constitute the major products. Table II gives representative product distributions generated using 1 and the heterogeneous hydrogen evolution catalyst, 3% Pt(0) on carbon.

TABLE II

Catalytic Production of Tri- and Tetra-substituted Alkenes from Alkanes

| Alkane Substrate | Product Yields, % Based on Total Organic Products (Based on H$_2$) | |
|---|---|---|
| 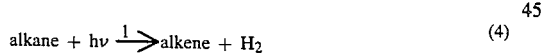 | | |
| | 91 (89) | |
| | 61 (65) | 25 (26) |
| | 5.4 (5.8) | 4.6 (4.9) |
| | overall yields: 96 (102) | |
| | 46 (46) | |
|  | 54 (46) | 11 (9) |
| | overall yields: 65 (55) | |
|  | 83 (73) | 17 (14) |
|  | overall yields: 100 (87) | |

TABLE II-continued
Catalytic Production of Tri- and Tetra-substituted Alkenes from Alkanes

| Alkane Substrate | Product Yields, % Based on Total Organic Products (Based on H$_2$) |
|---|---|
|  | 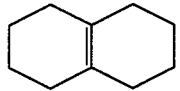 97 |

Reactions were carried out by irradiating highly purified acetonitrile solutions 3.13 mM in catalyst, [(H$_2$O)$_2$H]$_3$PW$_{12}$O$_{40}$·4.7H$_2$O (1) and 0.3 M in substrate alkane containing 3 mg of Pt(0) on carbon with 100w light source ($\lambda$ > 280 nm) at 25° C. for an average of 20 h. Yield given before the parenthesis in each case is the moles of that product divided by the moles of all detectable organic products × 100; yield given inside parenthesis in each case is the moles of that product divided by the moles of hydrogen produced × 100.

In Table II, product yields based both on the amount of hydrogen produced and the total quantity of all organic products formed are reported.

The regiospecificity in these reactions is nearly always for production of the most substituted and thermodynamically stable alkene. For example, alkanes capable of forming tetrasubstituted alkenes (e.g. 2,3-dimethylbutane) form the corresponding tetrasubstituted alkenes with high selectivity. Larger branched alkanes capable of generating many di- tri- and tetrasubstituted alkenes, still produce the tetrasubstituted products with reasonably high selectivities. Linear alkanes form other products in preference to alkenes in these systems. In acetonitrile, the principal nonolefinic byproducts are the N-alkylacetamide and/or alkyl methyl ketone. Although the relative thermodynamic stabilities of the alkenes formed is an important factor, it is not the only factor that dictates the relative yields of products in these reactions. The catalytic photochemical dehydrogenation of geometrically isomeric alkanes capable of forming the same tetrasubstituted alkene were examined. Different geometrical isomers give similar, but not identical ratios of alkene products and different ratios of olefinic to nonolefinic products. The dehydrogenation of cis- and trans-1,2-dimethylcyclohexane in Table II is exemplary. Likewise cis- and trans-decalin both give the tetrasubstituted internal olefin as the principal product, but the yield of the nonolefinic products was much higher for the trans-decalin.

It is reasonable from all the data given here and elsewhere that the novel substrate activation process in these catalytic dehydrogenation reactions involves removal of an electron from the alkane by the excited polyoxometalate. Both this redox process and the subsequent deprotonation of the alkane cation radical are partially product determining steps with respect to formation of alkene(s).

The energetics of equation 4 are of much interest. The $\Delta H°$ for this process is as high as +35 kcal/mol for some alkanes. As shown in FIG. 1, the relative rates of reaction vary substantially with alkane structure and correlate roughly with ionization potential. Although the quantum yields for production of the reduced polyoxotungstate intermediates (P$_r$ in equations 6 and 7) approach 0.1 at 350 nm for the most reactive branched alkanes, they are less than 0.01 for the least reactive systems, such as 2,2-dimethylbutane.

The dramatic changes in the heteropoly acid photochemical action spectra with respect to organic substrate oxidation and the parallel changes in the absorption spectra, induced by the presence of several dipolar organic substrates are not induced by the alkane substrates. Small spectral shifts of these kinds are produced, however, by high concentrations of alkene. Whereas 1 forms colorless solutions in water, alcohols, or acetonitrile with or without alkane, this complex does form colored (pale yellow) photosensitive solutions in the presence of alkenes. Although the inventor has been successful at isolating and characterizing the colored photosensitive intermolecular complexes between dipolar organic substrates and heteropoly acids by $^{183}$W, $^{17}$O and $^{31}$P NMR, X-ray crystallography, and several other methods, characterization of the colored photosensitive alkeneheteropoly complexes has not yet been possible. The ability of the latter materials to crystallize is very low.

Three side reactions pertaining to the chemistry described here warrant discussion. First, the principal process that decreases the yields of the photosynthetic products, alkene(s) and hydrogen, is the reverse hydrogenation of the alkene once formed, the reverse of equation 4. This process can begin to become important after one turnover. The continuous removal of the hydrogen formed minimizes the reverse of equation 4, greatly decreasing the quantity of N-alkylacetamide and alkyl methyl ketone byproducts formed, and increases the net efficiency of these processes.

The second side reaction of note involves the protons associated with the polyoxometalate catalyst, 1. In the systems described herein, 1 functions not only in its photosensitization and its reversible redox capacities, but also as an efficient acid catalyst. This complex is reasonably acidic and can catalyze the hydration of the product alkenes by the few water molecules present initially as the water of solvation associated with 1 (equation 8).

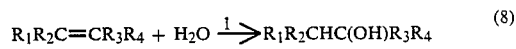

(R$_1$R$_2$R$_3$, and R$_4$ = organic group or hydrogen)

Heteropoly acids have been reported to be effective acid catalysts in several transformations. It is also known that the water molecules of solvation associated with 1, and other heteropoly acids are very important to the solubility of these complexes in polar or hydrogen-bonding solvents. Removal of the water molecules of solvation of heteropoly acids results in their precipitation from anhydrous polar organic solvents such as acetonitrile. For the production of some of the tetrasubstituted alkenes by catalytic photosynthetic dehydrogenation, equation 8 proceeds to the point where the catalyst, 1, precipitates or crystallizes from solution. The point at which the polyoxotungstate precipitates depends on both the degree of hydration of the starting polyoxotungstate and quantity of alkene generated during the course of the reaction. For example, when 4.54×10$^{-3}$ mol of 2,3-dimethylcyclohexene-1 is added to an acetonitrile solution containing 3.5×10$^4$ mol of 1, a white precipitate forms which has a weight of 29% the weight of the original quantity of polyoxotungstate. If less than this quantity of 2,3-dimethylcyclohexene-1 is added, no precipitate will form. The introduction of activated 4A molecular sieves also results in production of the same precipitate or crystals. The precipitate or crystals generated by dehydration via either of these processes resolvate and redissolve, and complete catalytic activity is restored if a few equivalents of water are subsequently added to the system.

The third side reaction of note involves the precipitation of the catalyst if excessive amounts of hydrogen build up. If a small quantity of Pt(0) or other hydrogen activation catalyst is added to the reactions, the reverse of equation 7, reduction of 1 by the $H_2$ evolved, can become rapid. If under these conditions, several equivalents of hydrogen gas per equivalent of 1 are generated, polyoxometalates reduced by more than one electron begin to form. These highly charged species are sufficiently insoluble that they precipitate from solution, slowing or terminating the net photosynthetic reaction.

The homogeneous catalytic photochemical dehydrogenation of alkanes by polyoxometalates, and in particular heteropolytungstic acids, provides the first method of converting completely saturated hydrocarbons into the corresponding maximally substituted alkenes and hydrogen gas. These processes accomplish both potentially useful synthetic transformations and convert substantial quantities of radiant energy into chemical energy ($\Delta H°$ can be as high as $+35$ kcal/mol). As such they qualify as effective photosynthetic processes.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for functionalizing alkanes, which comprises:
   (a) combining one or a mixture of alkanes with a photochemically active polyoxometalate compound to obtain a reaction medium;
   (b) allowing said photochemically active polyoxometalate compound to catalyze homogeneously functionalization of said alkane in the presence of visible or ultraviolet light wherein said functionalization is carried out by said polyoxometalate in an excited state and produces a reduced polyoxmetalate; and
   (c) obtaining said functionalized alkane from said reaction medium.

2. The method of claim 1, wherein said alkane is a $C_{1-100}$ straight chain, branched or cyclic alkane.

3. The method of claim 2, wherein said alkane is a $C_{2-50}$ straight chain, branched or cyclic alkane.

4. The method of claim 2, wherein said alkane is a $C_5$ to $C_{12}$ cyclic alkane.

5. The method of claim 1, wherein said polyoxometalate has one of the following formulas:
   (i) $[XW_xMo_yV_zO_{40}]Q_aM_b$; wherein $x+y+z=12$, and $(a+b)=3$ to $12$,
   (ii) $[X_2W_lMo_mV_nO_{62}]Q_cM_d$; wherein $l+m+n=18$, and $(c+d)=6$ to $15$,
   (iii) $[X_5W_pMo_qV_rO_{110}]Q_eM_f$; wherein $p+q+r=30$, and $(e+f)=14$ to $20$,
   (iv) $[XW_sMo_tV_uO_{39}]Q_gM_h$; wherein $s+t+u=11$, and $(g+h)=7$ to $15$,
   (v) $[XW_vMo_wV_{xx}O_{34}]Q_iM_j$; wherein $v+w+xx=9$, and $(i+j)=9$ to $15$,
   (vi) $[(M')XW_sMo_tV_uO_{39}]Q_kM_{aa}$; wherein $s+t+u=11$, and $(k+aa)=4$ to $15$,
   (vii) $[XW_vMo_wV_{xx}O_{34}]_2(M')_3Q_{bb}M_{cc}$; wherein $v+w+xx=9$, and $(bb+cc)=10$ to $18$,
   (viii) $[XW_{yy}Mo_{zz}V_{ll}O_{34}]_2(M')_4Q_{dd}M_{ee}$; wherein $yy+zz+ll=9$, and $(dd+ee)=10$ to $18$,
   (ix) $[H_2W_{12}O_{40}]Q_{ff}M_{gg}$; wherein $(ff+gg)=6$,
   (x) $[W_{10}O_{32}]Q_{hh}M_{ii}$; wherein $(hh+ii)=4$,
   (xi) $[V_{10}O_{28}]Q_{jj}M_{kk}$ wherein $(jj+kk)=6$,
   (xii) $(NH_4^+)_6[Mo_7O_{24}]$, wherein X is selected from the group consisting of transition metal di and trivalent cations and tri, tetra and pentavalent non-transition metal cations; Q is a quaternary ammonium, phosphonium or arsonium salt, $R_4N^+$, $R_4P^+$ or $R_4As^+$, wherein R is a $C_{1-30}$ straight chain, branched or cyclic alkyl group or a $C_{6-30}$ aromatic group; each of $M_{b,d,f,m,h,j,ar,cc,ee,gg,ii,kk}$ is $H^+$, $NH_4^+$, or any non-transition metal, transition metal, lanthanide or stable actinide ion, and M' is a transition metal with greater than 0 d electrons.

6. The method of claim 5, wherein X is selected from the group consisting of $Co^{2+}$, $Fe^{3+}$, $P^{5+}$, $As^{5+}$, $Si^{4+}$, $Ge^{4+}$, and $B^{3+}$.

7. The method of claim 5, wherein each $M_{b\text{-}kk}$ is selected from the group consisting of $H^+$, $NH_4^+$, $Li^+$, $Na^+$, $K^+$, $Mg^{2+}$, $Cr^{3+}$, $Fe^{3+}$, $Fe^{2+}$, $Co^{2+}$, low spin $Co^{3+}$, $Ni^{2+}$, $Zn^{2+}$, $La^{3+}$, $Eu^{2+}$, and stable actinide ions.

8. The method of claim 7, wherein each $M_{b\text{-}kk}$ is $H^+$ or $NH_4^+$.

9. The method of claim 5, wherein W is the predominant transition metal element in said formulas (i)–(xi).

10. The method of claim 5, wherein W is the sole element transition metal in said formulas (i)–(xi).

11. The method of claim 1, wherein said catalyst is a member selected from the group consisting of $H_3PW_{12}O_{40}$, $H_3AsW_{12}O_{40}$, $H_4SiW_{12}O_{40}$, $H_4GeW_{12}O_{40}$, $(n\text{-}Bu_4N)_4W_{10}O_{32}$, $H_5BW_{12}O_{40}$, $H_6P_2W_{18}O_{62}$, $(NH_4^+)_6[P_2W_{18}O_{62}]$, and $(NH_4^+)_6[Mo_7O_{24}]$.

12. The method of claim 11, wherein said catalyst is hydrated.

13. The method of claim 1, wherein said light has a wavelength of from 210 nm up to 400 nm.

14. The method of claim 1, wherein said reaction is conducted in the presence of $O_2$ or air.

15. The method of claim 1, wherein said reaction is conducted with a solvent selected from the group consisting of acetonitrile, water and t-butanol.

16. The method of claim 1, wherein said reaction medium further comprises a catalytic quantity of Pt(0) and wherein said Pt(0) oxidizes the reduced polyoxometalate back to its original form with evolution of hydrogen.

* * * * *